United States Patent [19]

Foote

[11] Patent Number: 4,739,662
[45] Date of Patent: * Apr. 26, 1988

[54] ULTRASONIC PARTICULATE SENSING

[75] Inventor: Kenneth G. Foote, Laksevaag, Norway

[73] Assignee: Micro Pure Systems, Inc., Smithfield, R.I.

[*] Notice: The portion of the term of this patent subsequent to Jul. 9, 2002 has been disclaimed.

[21] Appl. No.: 856,051

[22] Filed: Apr. 25, 1986

Related U.S. Application Data

[63] Continuation of Ser. No. 681,108, Dec. 12, 1984, abandoned, which is a continuation of Ser. No. 387,741, Jun. 11, 1982, Pat. No. 4,527,420.

[51] Int. Cl.$^4$ ............................................. G01N 29/00
[52] U.S. Cl. ...................................... 73/599; 73/61 R; 73/865.5
[58] Field of Search ................... 73/432 PS, 28, 32 A, 73/61 R, 599, 627, 628, 865.5

[56] References Cited

U.S. PATENT DOCUMENTS

| | | | |
|---|---|---|---|
| 3,178,940 | 4/1965 | Dahlke et al. | 73/861.26 |
| 3,208,286 | 9/1965 | Richard | 73/432 PS |
| 3,774,717 | 11/1973 | Chodorow | 73/61 R |
| 4,112,773 | 9/1978 | Abts | 73/61 R |
| 4,339,944 | 7/1982 | Abts et al. | 73/61 R |
| 4,412,451 | 11/1983 | Uusitalo et al. | 73/432 PS |

OTHER PUBLICATIONS

Rayleigh, *Theory of Sound*, 1945, vol. II, pp. 272-284.

*Primary Examiner*—John Chapman

[57] ABSTRACT

An apparatus for identifying and determining the size of particulates in a flowing fluid by detecting the portion of an ultrasonic pulse scattered from a particulate at a preselected angle, converting the results into density and elasticity-related values and comparing the values with measured or computed values for known particulates.

1 Claim, 1 Drawing Sheet

ULTRASONIC PARTICULATE SENSING

This application is a continuation of application Ser. No. 681,108, filed Dec. 12, 1984, abandoned; which is a continuation of application Ser. No. 387,741, filed June 11, 1982, now U.S. Pat. No. 4,527,420.

FIELD OF THE INVENTION

This invention relates to a method of identifying and determining the size of particulates in a flow.

BACKGROUND OF THE INVENTION

In certain chemical processes, e.g., the fabrication of semiconductors, it is important that the complex chemical fluids used have the proper composition. For example, in one such process, the presence of small nickel or iron particles may be necessary, but small particles of aluminum may destroy the end product. In another process, it may be critical to distinguish between air bubbles and oil droplets for the same reason. Also, the size of a certain type of particulate may be the important factor in some processes.

SUMMARY OF THE INVENTION

I have discovered that particulates in a fluid can be identified by sending an ultrasonic pulse across the fluid, measuring the amplitude of the portion of the pulse scattered from a particulate at a preselected angle, converting the amplitude into density and elasticity-related values and comparing the values with those for known particulates. The relative size of the particulate is simultaneously determined from the magnitude of the scattered signal.

In preferred embodiments, a transducer sends an ultrasonic pulse across a fluid flow, and the pulse is partially scattered when it strikes a particulate in the fluid. The amplitude of the scattered portion of the pulse is measured by two transducers at locations which will receive scattered energy at different angles, and density and elasticity-related values for the particulate are determined based upon the amplitudes and the preselected angles at which the scattered portions of the pulse are received. To identify the particulate, these values are compared with those for known particulates by plotting the values, while a comparison of the amplitude measurement provides a determination as to particulate size.

PREFERRED EMBODIMENTS

We turn now to the structure and operation of the preferred embodiments, after first briefly describing the drawings.

Drawings

Structure

Figure 1:
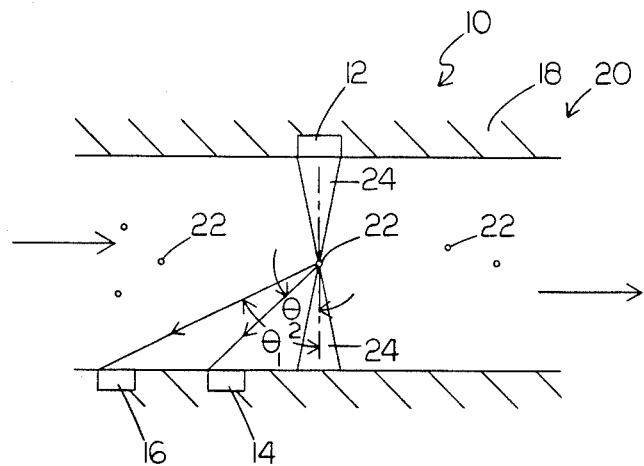
FIG. 1 is a cross-sectional view of the apparatus of the preferred embodiment of the invention.

Referring to FIG. 1, there is shown a scattering detecting apparatus at 10. Apparatus 10 generally comprises a transmitting transducer 12 and a pair of receiving transducers 14, 16.

Transducer 12 is mounted in a sidewall 18 of a fluid-carrying conduit 20 so as to direct a focused pulse of ultrasonic energy across the flow, which contains a number of particulates 22 of different types. The focal point is arranged to be at the approximate midpoint of the conduit 20. Receiving transducer 14 is mounted in the portion of the sidewall 18 generally opposite transmitting transducer 12 but far enough upstream as to be outside the primary area 24 of the focused ultrasonic pulse. Receiving transducer 16 is further upstream than transducer 14. Both receiving transducers 14, 16 are however, close enough to the primary area 24 of the focused pulse to be in the transducer's shadow zone, i.e., a nearby, surrounding area which receives a greatly reduced portion of the ultrasonic energy from the pulse. The transducers are the same as that disclosed in Abts U.S. Patent application Ser. No. 187,615, filed Sept. 15, 1980, which is commonly assigned with this application and incorporated herein by reference.

The transducers are connected to the electronic pulsing and receiving devices (not shown) which are described in Abts U.S. Pat. application Ser. No. 360,404, filed Mar. 22, 1982, which is also commonly assigned with this application and incorporated herein by reference.

Operation

In operation, transmitting transducer 12 sends a focused pulse of ultrasonic energy across the flow, and a particulate 22 in the primary area 24 of the focused pulse will reflect some of the energy back to the transducer 12. At the same time, however, the particulate will also scatter a portion of the pulse that strikes it, and the scattered energy field radiates in all directions from the particulate. This scattered energy field is not uniform. Instead, its amplitude at any given place is a function (for solid particles) of the density of the particle and its shear and longitudinal waves, which are related to the elasticity of the particle. For air bubbles and liquid droplets the amplitude is a function only of the density and the longitudinal waves, as these particulates do not support shear waves. In both cases, each individual type of particulate creates its own unique scattered energy field.

Some of the scattered energy is detected by the two receiving transducers 14, 16, and the peak amplitude of detected energy is measured for each transducer. The peak amplitude is a voltage, and it is converted into a pressure amplitude by the following equation:

$$P = VC$$

where V is the measured peak amplitude voltage and C is the calibration constant. The calibration constant is frequency dependent, but as only one frequency is used, i.e., 15 MHz for the preferred embodiment, it can be easily measured or computed for the system.

The pressure amplitude, P, is then converted into a scattering amplitude or scattering strength, F, by the following equation:

$$F = Pd/Po$$

where d is the distance between the transducer and the particulate, and Po is the pressure amplitude of the wave incident on the particulate, which is a function of the transducer used. As an approximation, d may be measured from the midpoint of the conduit directly beneath the transmitting transducer.

The scattering amplitude F is related to the angle of incidence in the following manner:

$$F = \alpha + B \cos \theta$$

where $\alpha$ and B are constants related to the density and elasticity of the particulate, and $\theta$ is the angle of scattering measured from the forward direction of the initial pulse, as shown in FIG. 1. As there are two measurements for F and the $\theta_1$ and $\theta_2$ are known for the receiving transducers 14, 16, $\alpha$ and B may be computed, and these values will be different for different particulates. For example, nickel has a $\alpha$ of 0.330 and a B of $-0.420$, while aluminum has a $\alpha$ of 0.324 and a B of $-0.266$. As an additional distinction, most metals have a positive $\alpha$ and a negative B, while most liquids have a negative $\alpha$ and a positive or negative B. Silicone rubber, on the other hand, has both values negative. The particulates are thus identified by comparing these values derived from the measured peak amplitudes with the measured or computed values for known particulates.

Figure 3:
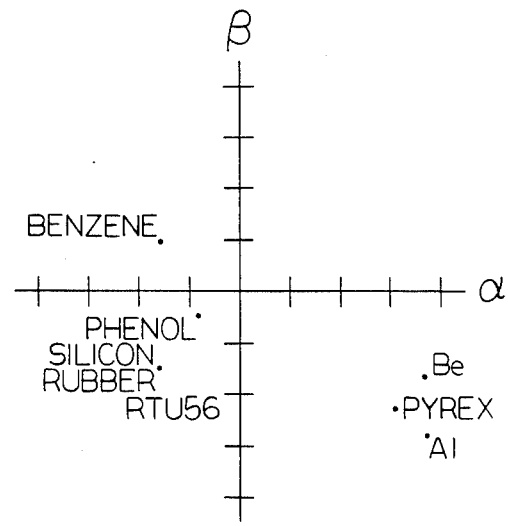
FIG. 3 is a plot of amplitude-based values for a number of different types of particulates.

The procedure is repeated a number of times to identify all of the different particulates in the flow and to obtain repetitive readings for different particulates of the same type. The latter eliminates the possibility of a misidentification based on a single, erroneous reading. The $\alpha$ and B results are plotted in a graph, such as that of FIG. 3, which provides a visual representation of the very different values obtained from several particulates. The size of the particulate is directly related to the magnitude of the scattering amplitude F so that when the particulate is identified, its size is also determined by referring back to the computed scattering amplitude. For some uses, however (e.g., where only a couple of known particulates of a known size may be present), the scattering amplitude alone may serve to identify the particulate. (Usually, however, a number of different particulates might have the same amplitude F at a given angle.) Also, if there is only one type of unknown particulate in a flow, the $\alpha$ and B need not be computed for each scattering amplitude, F. Instead, the average of a number of scattering amplitudes may be used to compute a single $\alpha$ and B value.

OTHER EMBODIMENTS

Figure 2:
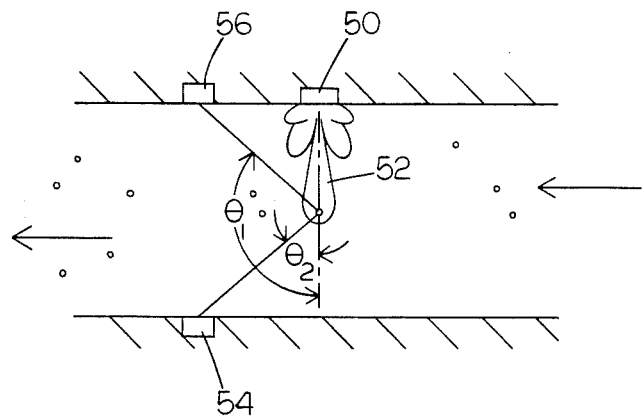
FIG. 2 is a cross-sectional view of the apparatus of another preferred embodiment.

In another embodiment of this invention, as shown in FIG. 2, transducer 50 produces an unfocused pulse having a principal lobe 52. The receiving transducers 54, 56 are located in the minor sidelobe regions, and in this embodiment, they are disposed across from each other. As shown by FIG. 2, the angles $\theta_1$ and $\theta_2$ for each are substantially different. The operation of this embodiment is as described above.

It is also possible to use additional receiving transducers in the system, but the $\alpha$ and B values in such a system would be determined by a least-mean-squares method. It is also possible to use the transmitting transducer as a receiving transducer.

Other variations will occur to those skilled in the art. What I claim is:

1. An apparatus for identifying particulates in a flowing fluid comprising:

means for transmitting ultrasonic energy in the form of a pulse into a flow comprising a first transducer, means for detecting the magnitude of the energy scattered when the pulse strikes a particulate in the flow, said means for detecting comprising a second transducer being disposed opposite said first transducer at one selected angle other than zero degrees with respect to said first transducer and a point across the flow directly opposite said first transducer, said second transducer receiving energy scattered from any particulate in the flow at said selected angle, the sole output of said apparatus being the magnitude of the scattered energy detected by said second transducer at said selected angle, means for comparing the magnitude of the scattered energy detected by said second transducer at said selected angle with the magnitude of scattered energy from known particulates detected at said selected angle whereby the particulate from which the energy is scattered may be identified.

* * * * *